United States Patent
Musa et al.

(10) Patent No.: US 11,304,955 B2
(45) Date of Patent: Apr. 19, 2022

(54) SMALL-MOLECULE POVIDONE ANALOGS IN COAMORPHOUS PHARMACEUTICAL PHASES

(71) Applicant: ISP INVESTMENTS LLC, Wilmington, DE (US)

(72) Inventors: Osama M. Musa, Bedminster, NJ (US); Jonathan W. Steed, Durham (GB); David Berry, Eaglescliffe (GB); Melissa J. Goodwin, Helgelo (NL)

(73) Assignee: ISP INVESTMENTS LLC, Wilmington, DE (US)

(*) Notice: Subject to any disclaimer, the term of this patent is extended or adjusted under 35 U.S.C. 154(b) by 10 days.

(21) Appl. No.: 16/620,831

(22) PCT Filed: Jun. 11, 2018

(86) PCT No.: PCT/US2018/036874
§ 371 (c)(1),
(2) Date: Dec. 9, 2019

(87) PCT Pub. No.: WO2018/227179
PCT Pub. Date: Dec. 13, 2018

(65) Prior Publication Data
US 2020/0188408 A1    Jun. 18, 2020

Related U.S. Application Data

(60) Provisional application No. 62/517,435, filed on Jun. 9, 2017.

(51) Int. Cl.
| | | |
|---|---|---|
| A61K 47/22 | (2006.01) | |
| A61K 31/135 | (2006.01) | |
| A61K 31/136 | (2006.01) | |
| A61K 31/519 | (2006.01) | |
| A61K 31/55 | (2006.01) | |
| A61K 31/27 | (2006.01) | |
| A61K 31/44 | (2006.01) | |
| A61K 31/192 | (2006.01) | |
| A61K 31/155 | (2006.01) | |
| A61K 31/14 | (2006.01) | |
| A61K 31/196 | (2006.01) | |
| A61K 31/41 | (2006.01) | |
| A61K 31/381 | (2006.01) | |

(52) U.S. Cl.
CPC ............ *A61K 31/55* (2013.01); *A61K 31/135* (2013.01); *A61K 31/136* (2013.01); *A61K 31/14* (2013.01); *A61K 31/155* (2013.01); *A61K 31/192* (2013.01); *A61K 31/27* (2013.01); *A61K 31/381* (2013.01); *A61K 31/41* (2013.01); *A61K 31/44* (2013.01); *A61K 31/519* (2013.01); *A61K 47/22* (2013.01)

(58) Field of Classification Search
CPC ...... A61K 47/22; A61K 31/55; A61K 31/135; A61K 31/136; A61K 31/14; A61K 31/155; A61K 31/192; A61K 31/196; A61K 31/27; A61K 31/381; A61K 31/41; A61K 31/44; A61K 31/519
See application file for complete search history.

(56) References Cited

U.S. PATENT DOCUMENTS

| | | |
|---|---|---|
| 2005/0182219 A1 | 8/2005 | Meyer et al. |
| 2007/0219692 A1 | 10/2007 | Fort et al. |
| 2016/0324773 A1 | 11/2016 | Paiement et al. |

OTHER PUBLICATIONS

Dengale et al. Advanced Drug Delivery Reviews 2016, 100, 116-125.*
Goodwin et al. Cryst. Growth Des. 2018, 18, 701-708.*
Hydration Behavior of Polylactam Clathrate Hydrate Inhibitors and Their Small-1-3 Molecule Model Compounds, Crystal Growth & Design, Apr. 21, 2017 (Apr. 21, 2017), vol. 17, pp. 3236-3249.
International Search Report of PCT/US18/36874 published on Dec. 13, 2018 under publication No. W020180227179.

* cited by examiner

*Primary Examiner* — Irina Neagu
(74) *Attorney, Agent, or Firm* — William J. Davis; Nathalie Tietcheu

(57) ABSTRACT

An amorphous dispersion comprises bis(vinylcaprolactam) and an active pharmaceutical ingredient.

1 Claim, 4 Drawing Sheets

SMALL-MOLECULE POVIDONE ANALOGS IN COAMORPHOUS PHARMACEUTICAL PHASES

SUMMARY OF THE INVENTION

The crystallization inhibitor polyvinylpyrrolidone (PVP) is commonly used as a stabilizer in the formation of amorphous polymer dispersions of poorly soluble pharmaceuticals. Disclosed herein are small-molecule bis(lactams) as coformers in the stabilization of coamorphous pharmaceutical phases. The dimer of N-vinyl(caprolactam), (bis)vinylcaprolactam (bisVCap, 3) was found to be particulary effective coamorphous-former at relatively low loading for carisoprodol, carbamazepine, isoniazid and ROY.

BRIEF DESCRIPTION OF THE DRAWINGS

Further embodiments of the preset application can be understood with the appended figures.

DETAILED DESCRIPTION OF THE INVENTION

Figure 1A:
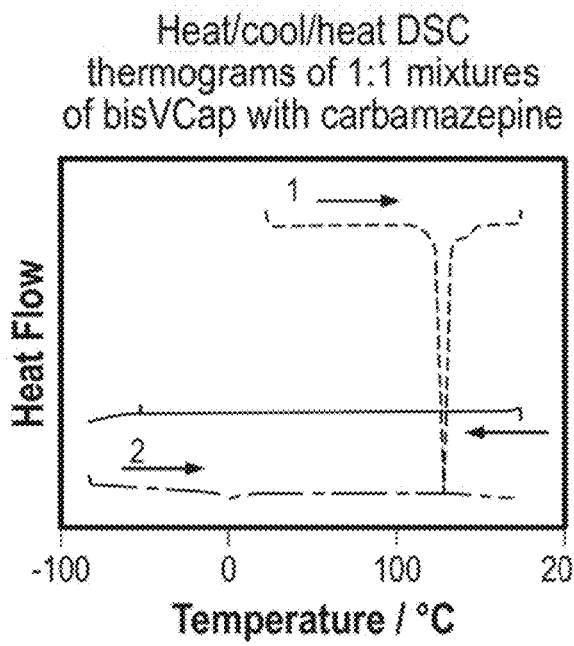
FIG. 1 shows Heat/cool/heat DSC thermograms of 1:1 mixtures of bisVCap with a) carbamazepine, b) carisoprodol, c) isoniazid and d) ROY (exotherm up).
Figure 1B:
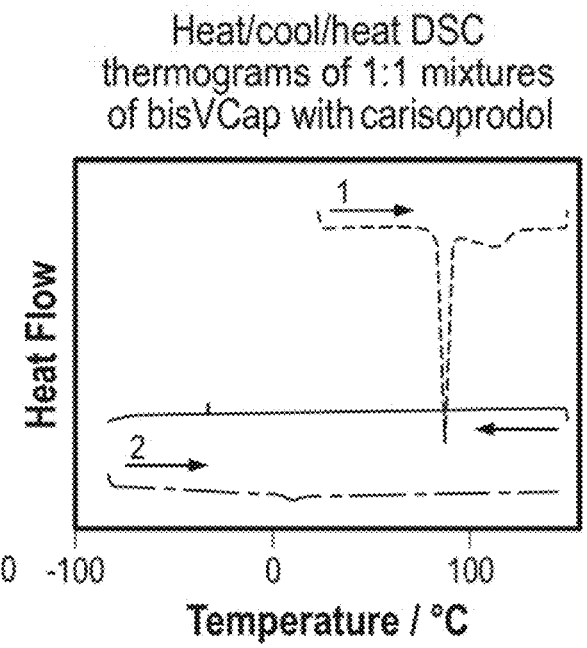
Figure 1C:
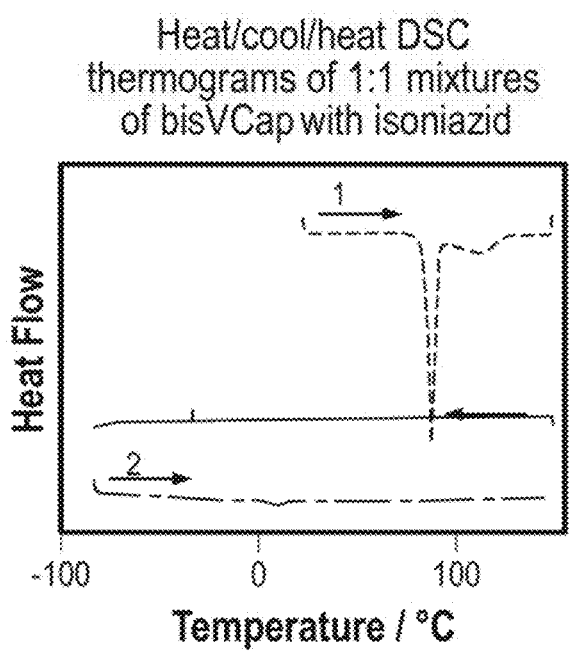
Figure 1D:
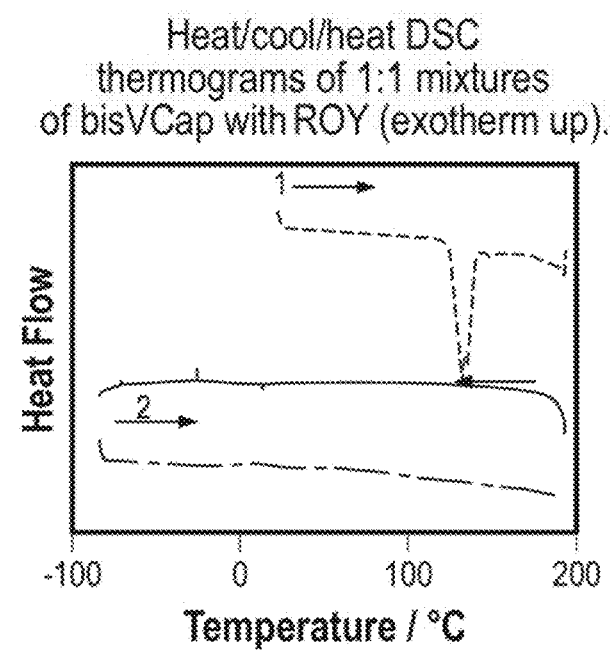
Figure 2A:
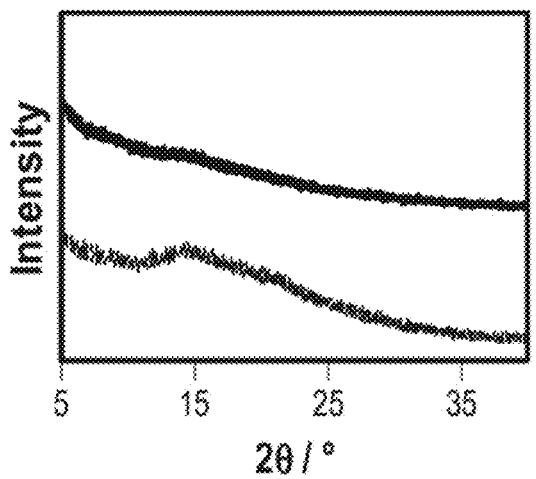
FIG. 2 shows XRPD diffractograms of a) carbamazepine with bisVCap in 1:1 and 2:1 molar ratios, b) carisoprodol with bisVCap in 1:1 and 2:1 molar ratios, c) isoniazid with bisVCap in 1:1 and 2:1 molar ratios and d) ROY with bisVCap in 1:1 and 2:1 molar ratios.
Figure 2B:
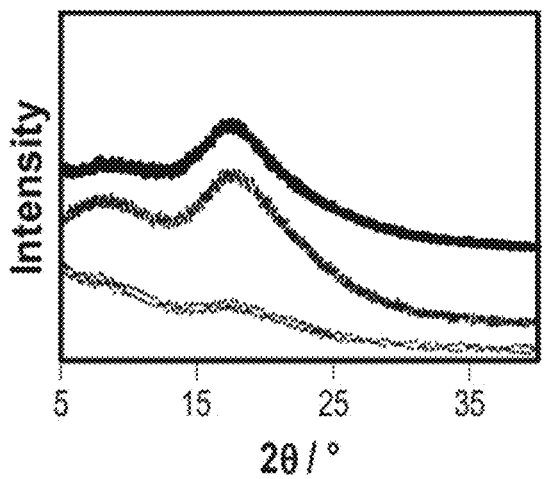
Figure 2C:
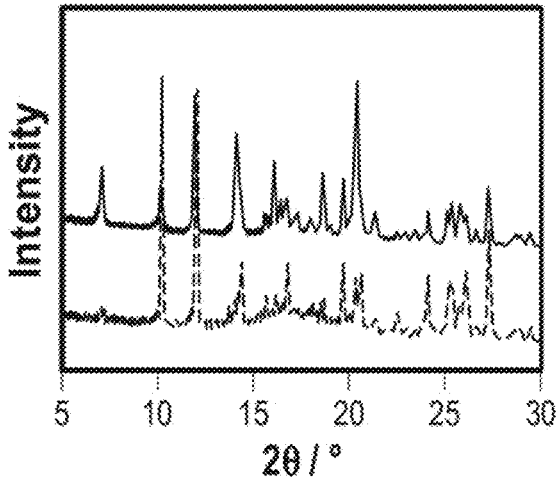
Figure 2D:
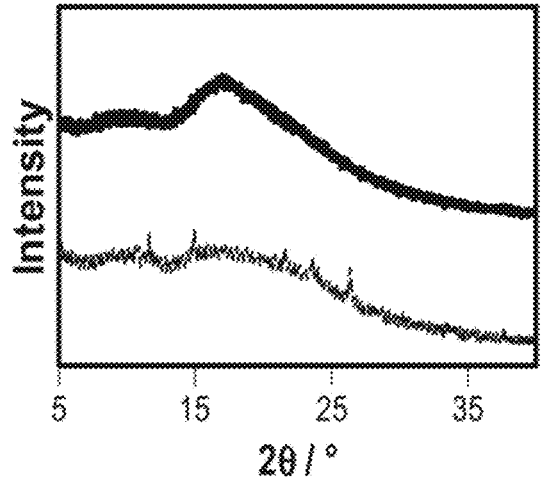

A major challenge in the development of new pharmaceutical products is drug bioavailability, particularly given the increasing trend towards more hydrophobic active pharmaceutical ingredients (APIs). One of the main issues affecting bioavailability is the solubility of the drug in water. Cocrystallization, salt formation and the use of metastable polymorphs have been among the methods employed to help drug solubility and dissolution rate. There is also increasing interest in amorphous drugs and a number of formulations containing amorphous APIs are now commercially available (e.g. zafirlukast, cefuroxime axetil, quinapril hydrochloride and nelfinavir mesylate). As the amorphous state is less thermodynamically stable than the crystal, amorphous materials are generally (initially) more water soluble and hence more bioavailable. However, both preparing and stabilizing amorphous materials is often challenging. Amorphous materials can be chemically less stable than crystalline compounds, more hygroscopic and can display a tendency to convert to crystalline form over time. One way to help prevent crystallization, and both chemically and physically stabilize molecules in an amorphous form is the addition of a second component (coformer) to create a coamorphous mixture. Coamorphous materials are similar in concept to cocrystals, in that the second component is often complementary to the drug substance, but unlike cocrystals, the goal is to disrupt favorable interactions which promote crystal formation while promoting drug-coamorphous-former interactions to stabilize the API on a local level.

In addition to coamorphous phases, a variety of approaches have been used to stabilize amorphous drugs including inorganic and mesoporous materials such as silica, and polymer dispersions. One of the most common polymers used in amorphous dispersions is polyvinylpyrrolidone (PVP or povidone, 1). PVP is a very common formulation agent, stabilizer and viscosity enhancer with applications in hydrate inhibition chemistry, haircare, cosmetics, shampoos and drilling fluids as well as in the pharmaceutical sector. The highly polar lactam carbonyl group imparts excellent electron donor and hydrogen bond acceptor ability without significant hydrogen bond acidity. PVP is commonly used in drug formulation, often as a binding and bulking agent when making pills or for potentially creating delayed release formulation based on its thermal behavior. PVP is also highly effective as a stabilizing agent for amorphous forms of drugs in polymer dispersions. Common techniques for producing API-polymer dispersions include microprecipitation, ball milling, spray drying and hot-melt extrusion, although the inherent instability of polymer-amorphous API dispersions means that there are fewer commercial products of this type than might be expected. Though PVP is effective at stabilizing the amorphous form of a range of drugs, a high loading is often required to ensure long-term stability typically 50-80% by mass. Amorphous nifedipine requires a 1:4 ratio by mass with PVP, for example. While a high loading is not necessarily a problem for drugs with a small therapeutic index, drugs which require a larger dosage would either need pills too large to easily swallow or multiple pills per dose, neither of which are preferable for the patient. Moreover, ingestion of large amounts of PVP have been suggested to cause unpleasant side effects such as diarrhoea. The other main disadvantage of PVP is that it is hygroscopic. This property can reduce the shelf life of the product, either by water promoted degradation of the drug, or because water can cause a plasticizing effect in pills, aiding molecular mobility and crystallization. As a result, a less hygroscopic, lower loading alternative to PVP might be of potential utility. Small molecules such as pyrogallol, amino acids and drug mixtures have all previously been shown to be effective in stabilizing the amorphous form of pharmaceuticals by forming a coamorphous phase rather than a polymer dispersion.

Disclosed are stable coamorphous API phases with low molecular weight dilactams 3-8 derived from PVP (1) and the related polyvinylcaprolactam (PVCap, 2, derived from vinylcaprolactam, VCap). In this way, the advantageous properties of polymer-amorphous dispersions are combined with the advantageous features of small-molecule coamorphous phases.

Scheme 1. Chemical structures of PVP and PVCap and derivatives

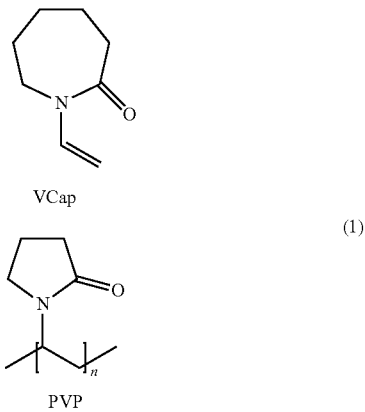

VCap (1)

PVP (2)
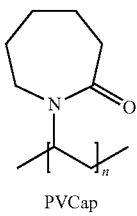
PVCap (3)
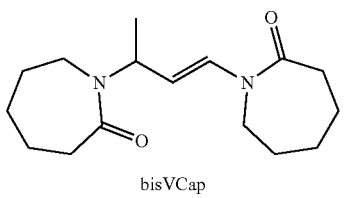
bisVCap (4)
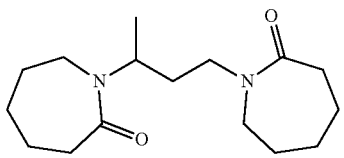
H₂bisVCap (5)
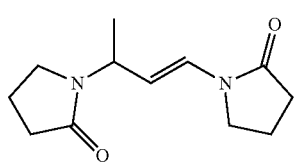
bisVP (6)
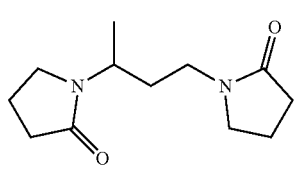
H₂bisVP (7)
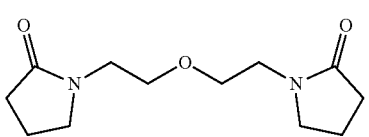
bisHEP (8)
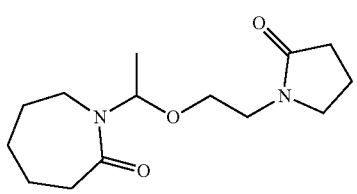
HEPVCap ROY Screening The highly polymorphic (5-methyl-2-[(2-nitrophenyl)amino]-3-thiophenecarbonitrile (ROY) was selected for initial screening for coamorphous phase formation with small molecule derivatives of PVP and PVCap. ROY is a precursor for the antipsychotic drug olanzapine, and is named after the red, orange and yellow colors of its ten solid forms. Due to its large number of polymorphs, ROY has been the focus of significant effort in expanding and controlling its solid form using novel methods of crystallization. While of academic interest, the crystallinity of compounds such as ROY can be disadvantageous in a pharmaceutical setting in cases of low dissolution rate.

Compounds 3-8 and VCap were all ground using a mortar and pestle in a 1:1 molar ratio with ROY. Comparative experiments were also undertaken in the same way with PVP (K12) (1) and PVCap (2) in a 1:1 ratio by mass with ROY. The samples were then placed on a microscope slide and covered with a thin, glass cover slip and heated using a hot stage optical microscope until all material had melted. The samples were then removed from the hot stage and allowed to cool to room temperature overnight. The cooled samples were examined under a microscope fitted with cross polarizing filters and assessed for crystallinity on the basis of birefringence.

As expected a control sample of ROY without any coformer readily crystallizes. It is interesting to note that under the conditions used, ROY crystallizes into three distinctive regions of different color suggesting that at least three different forms can be made from cooling the melt in this way. The Y04 form is initially produced, and cross-nucleates allowing different, faster growing forms to crystallize, resulting in a mixture of polymorphs from the same cooling crystallization.

Polarized optical microscope images were observed of ROY samples cooled overnight like a) ROY, b) ROY and PVP, c) ROY and PVCap, d) ROY and VCap, e) ROY and bisVCap, f) ROY and H₂bisVCap, g) ROY and bisVP, h) ROY and H₂bisVCap, i) ROY and bisHEP, j) ROY and HEPVCap.

Under the conditions of the experiment PVP would be expected to stabilize amorphous ROY and prevent crystallization. A co-melted sample of PVP and ROY which exhibits areas of different color suggesting that different phases may exist, though none of the phases show birefringence so are not crystalline and hence PVP is indeed an effective stabilizing agent for amorphous ROY. PVCap (which is not used as an amorphous stabilizer in the pharmaceutical industry) also prevents ROY crystallization and the sample remains amorphous and of a single phase. The unsaturated vinylcaprolactam dimer bisVCap (3), also gives a coamorphous phase with ROY. In contrast, all of the other small-molecule are less effective in preventing ROY crystallizing over time. While ROY itself crystallizes very quickly (within a few minutes) upon cooling, all of the small-molecule coformers slowed the crystallization process with crystals beginning to form within half an hour in the case of bisHEP, while the other coformer mixtures crystallized slowly overnight. Compounds 4-8 resulted in different combinations of crystal habitats and amorphous regions suggesting that these compounds influence polymorphic outcome but are ultimately ineffective at coamorphous phase formation. All of the samples were stored for a further two months at room temperature and periodically re-examined. No further changes were observed implying that all crystallization was complete within the first 24 hours and that the coamorphous phases formed by the two polymers and small molecule coformer bisVCap are stable for prolonged periods.

Screening of BisVCap and BisVP with a Range of Drugs

As bisVCap shows potential as an amorphous phase stabilizer for ROY, this compound along with bisVP was screened as a stabilizer for coamorphous phase formation with a range of other APIs. Thirteen drugs (including ROY) were chosen for screening based on availability, thermal stability and a range of chemical functionality, Scheme 2.

Scheme 2. APIs used in coamorphous screening.

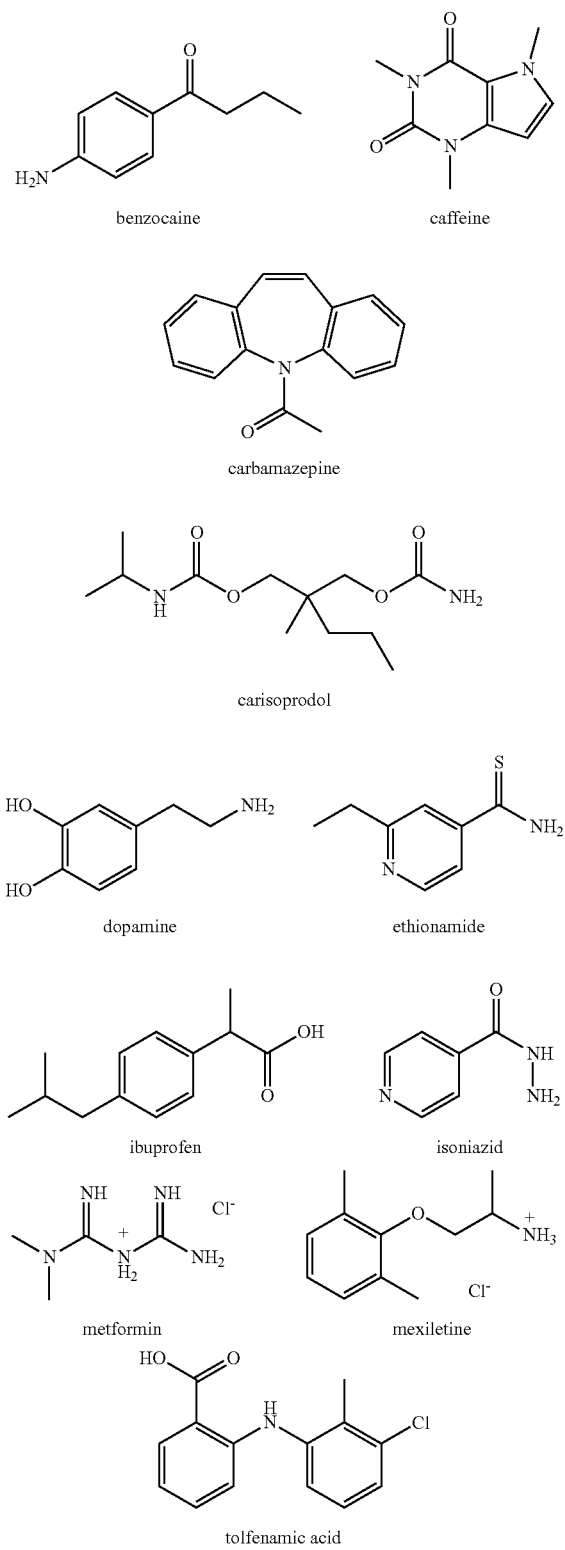

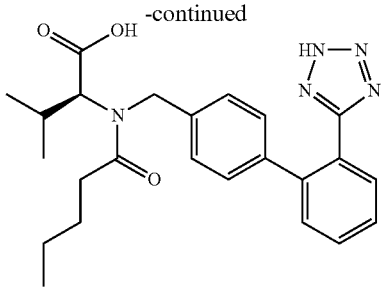

valsartan

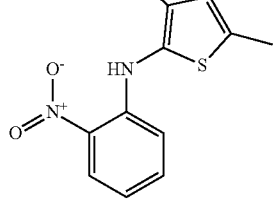

ROY

The drugs shown in Scheme 2 were ground together in a 1:1 mol ratio using a mortar and pestle with bisVCap and with bisVP before being heated on glass slides using a hot stage microscope until all material had melted. Control samples without lactam coformers were also prepared for comparison. The slides were then allowed to cool to room temperature. The samples were examined using polarized optical microscopy after storing them overnight and again two weeks after melting to assess their crystallinity. Polarized optical micrographs were observed. Valsartan, even on its own, remains amorphous, consistent with the fact that the drug is marketed in a stable amorphous form, although crystalline forms are also known but can be hard to prepare. The samples prepared using bisVP (which is itself an oil) all become viscous fluids, and hence are better described as liquid solutions rather than coamorphous solids. From the samples prepared with bisVCap, mixtures with benzocaine, caffeine and metformin crystallized overnight. In contrast mixtures of bisVCap with carbamazepine, carisoprodol, dopamine, ethionamide, ibuprofen, isoniazid, mexiletine and tolfenamic acid all resulted in materials which appear amorphous by polarized light microscopy after 18 hours at room temperature.

The API bisVCap combinations which appeared amorphous by polarized light microscopy were examined by differential scanning calorimetry (DSC). Ground 1:1 mixtures were heated past the melting point of the pure components (150-180° C.) in the DSC instrument, cooled to −85° C. and then subjected to a second heating cycle. The bisVCap-dopamine shows an endothermic peak in the second heating cycle corresponding to melting. As no crystallization was observed in the hot stage microscope experiment in which the sample is heated only once, it is possible that recrystallization occurs during the second heating cycle and hence the coamorphous phase is thermally unstable. The mixtures of bisVCap with ethionamide, tolfenamic acid, mexiletine and ibuprofen show a number of sharp and overlapping endothermic peaks on heating, which arise from decomposition of the samples. Ethionamide and mexiletine both decompose soon after their melting points as seen in the DSC thermographs of the individual components. DSC thermograms of ibuprofen and tolfenamic acid on the other hand indicate that they are thermally stable significantly above their melting points. The decomposition of the ibuprofen/bisVCap and tolfenamic acid/bisVCap mixtures on heating suggests that the interaction with bisVCap promotes degradation of the sample implying that bisVCap is not an ideal coamorphous former for these drugs. Mixtures of bisVCap with carisoprodol, carbamazepine, isoniazid and ROY all exhibit DSC thermographs lacking features assignable to decomposition, recrystallization or melting endotherms in the second heating cycle following coamorphous phase formation, FIG. 1. All four thermographs show an endothermic peak on initial heating which corresponds to the API sample melting. On cooling there are no exothermic peaks which would arise from recrystallization of the sample. During the second heating cycle all the thermographs show evidence for a glass transition consistent with the formation of amorphous material. The glass transitions all occur at or below room temperature, in approximately the region that would be expected based on the well-known '⅔ rule' which suggests that a glass transition is expected at around ⅔ of the temperature of the melting point of the crystalline material in Kelvin. Hence the new amorphous materials are not 'fragile' glasses.

The same heat-cool-heat cycles used in the DSC experiments were reproduced using a hot stage attached to a polarized light microscope for 1:1 mixtures of carisoprodol, carbamazepine, isoniazid and ROY with bisVCap. The results of the microscope experiments confirm coamorphous phase formation.

One major problem with PVP as an amorphous stabilizer is that often a large amount is required for stabilization of the amorphous phase. This often leads to very large pills or dosage forms which consist of multiple tablets. Thus further hot stage microscope and DSC experiments of bisVCap mixtures with carisoprodol, carbamazepine, isoniazid and ROY were performed with increasing drug:bisVCap ratios to determine the minimum ratio of coformer required to maintain the API in an amorphous state.

For the microscope experiments the drugs and bisVCap were ground in the desired ratio, heated until all the sample had melted then cooled back to room temperature and analyzed by polarized light microscopy. Carbamazepine, carisoprodol, isoniazid and ROY all showed no visible crystallization at a 2:1 drug:bisVCap molar ratio. Carisoprodol also did not show any visible crystallization at a 3:1 carisoprodol:bisVCap ratio. At 3:1 drug:bisVCap ratio carbamazepine, isoniazid and ROY all formed crystals overnight and carisoprodol formed crystals overnight from a 4:1 ratio. Heat-cool-heat DSC experiments were performed for the ratios which did not form crystals in the hot stage microscope experiments. Similar to the 1:1 ratios, no recrystallization event or melt during the second heating cycle is present in the DSC plots for 3:1 carisoprodol:bisVCap, 2:1 carbamazepine:bisVCap, 2:1 isoniazid:bisVCap or 2:1 ROY:bisVCap. This suggests that bisVCap is still an effective crystallization inhibitor at these ratios.

Coamorphous preparations were also examined by XRPD. The amorphous samples were prepared by melting the two components together and allowing the samples to cool to room temperature for 18 hours. Carbamazepine:bisVCap 2:1 and 1:1 and carisoprodol:bisVCap 3:1, 2:1 and 1:1 showed no Bragg peaks in the powder patterns, FIG. 2, consistent with the formation of a coamorphous phase. The 1:1 ratio of ROY:bisVCap also proved amorphous by X-ray diffraction, however the 2:1 ROY:bisVCap sample, while largely amorphous, exhibited some small Bragg peaks implying the beginning of crystallization of the API.

Neither isoniazid:bisVCap 2:1 or isoniazid:bisVCap 1:1 proved to be amorphous by XRPD. Comparison to powder patterns calculated from the literature crystal structures of isoniazid and bisVCap shows the material to be a mixture of the two known materials. While the observation of crystalline material by XRPD is not consistent with the optical microscopy and DSC data, and it is likely that the crystallization of this mixture is highly nucleation dependent and hence varies from sample-to-sample. After four weeks of being stored at room temperature, all samples except for 1:1 carisoprodol:bisVCap showed some evidence for crystallinity in their XRPD diffractograms, showing that over time they slowly revert to the more thermodynamically stable crystalline forms. The coamorphous form of 1:1 carisprodol:bisVCap is stable over the course of a month and hence is very promising for drug formulation.

Figure 3:
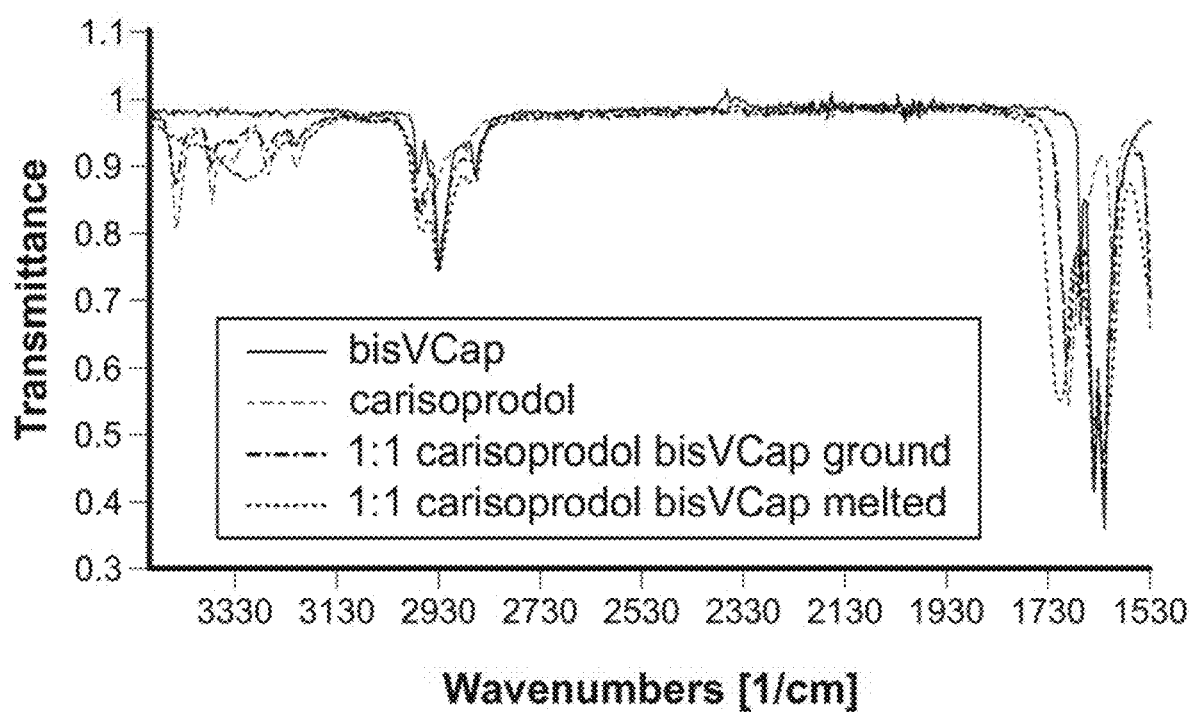
FIG. 3 shows IR spectra of bisVCap, carisoprodol and a 1:1 molar ratio of carisoprodol:bisVCap ground and melted.

IR spectra were recorded of carisoprodol, carbamazepine, isoniazid, ROY and bisVCap, as well as the 1:1, 2:1 and for carisoprodol 3:1 drug:bisVCap mixtures ground and co-melted. Simple grinding at room temperature of all four drugs with bisVCap did not result in any significant changes in the IR spectra, with the spectra being a simple superposition of those of the isolated components. Upon melting and cooling there are observable changes for carbamazepine, carisoprodol and isoniazid. For carisoprodol, FIG. 3, when the sample is melted and cooled the carbonyl peaks of bisVCap at 1622 $cm^{-1}$ and 1640 $cm^{-1}$ become much broader and less well-defined, an observation consistent with the formation of amorphous material. The carbonyl peak for the carisoprodol broadens and also shifts from 1690 $cm^{-1}$ to 1708 $cm^{-1}$. This suggests that the carbonyl bonds are becoming stronger so less involved in any intermolecular bonding. The bands between 3475-3180 $cm^{-1}$ which are associated with the N—H stretches of the carbamate groups, become a single broad peak in the spectrum of the cooled sample after melting, where in pure carisoprodol there were four sharp, distinct peaks. Upon increasing the ratio of carisoprodol:bisVCap from 1:1 to 2:1 to 3:1 there is no significant change in the position of any of the bands. The changes in the IR spectra of the co-melted carisoprodol-bisVCap mixtures imply that there are changes in the local environment of the carisoprodol molecules which affect its crystallization.

Similarly, both carbamazepine and isoniazid show a large degree of broadening of the carbonyl peaks in the spectra of the cooled samples after melting while there is no change in the co-ground sample. The spectra of cooled melts of samples of carbamazepine:bisVCap and isoniazid:bisVCap showed no change between the 1:1 and 2:1 ratios. On the other hand, ROY exhibits no change in peaks in the IR spectra in the ground or melted samples at either a 1:1 or 2:1 ROY:bisVCap ratio. Even when melted and cooled, the spectrum for ROY/bisVCap is a mixture of the bisVCap and ROY spectra, with no shifts in the peaks of interest. This suggests that unlike carbamazepine, carisoprodol and isoniazid, which see significant changes to the local environment, the stabilization of the amorphous form in ROY/bisVCap does not arise from local intermolecular interactions.

Figure 4A:
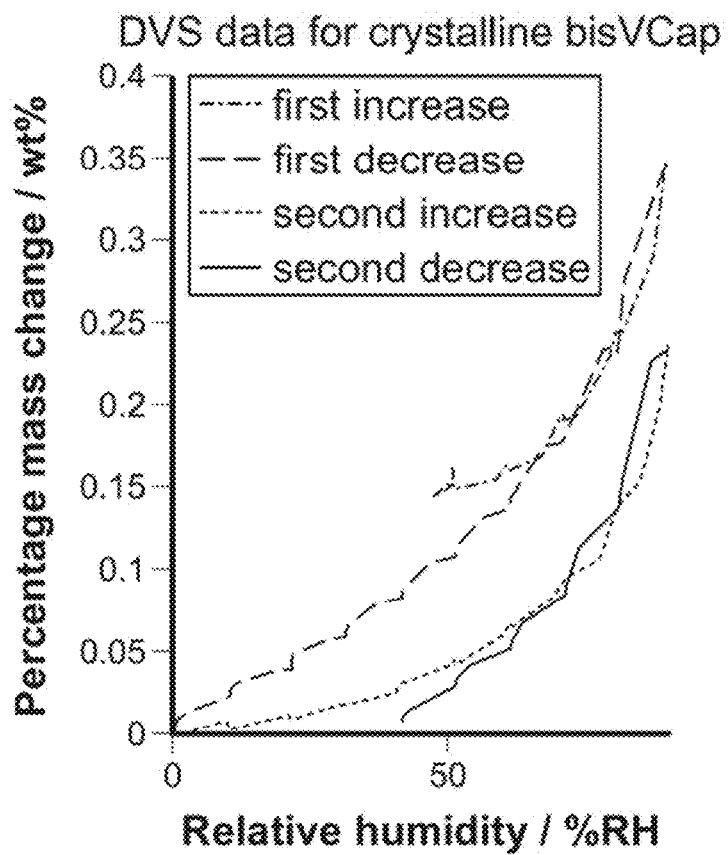
FIG. 4 shows DVS data for a) crystalline bisVCap and b) amorphous bisVCap.
Figure 4B:
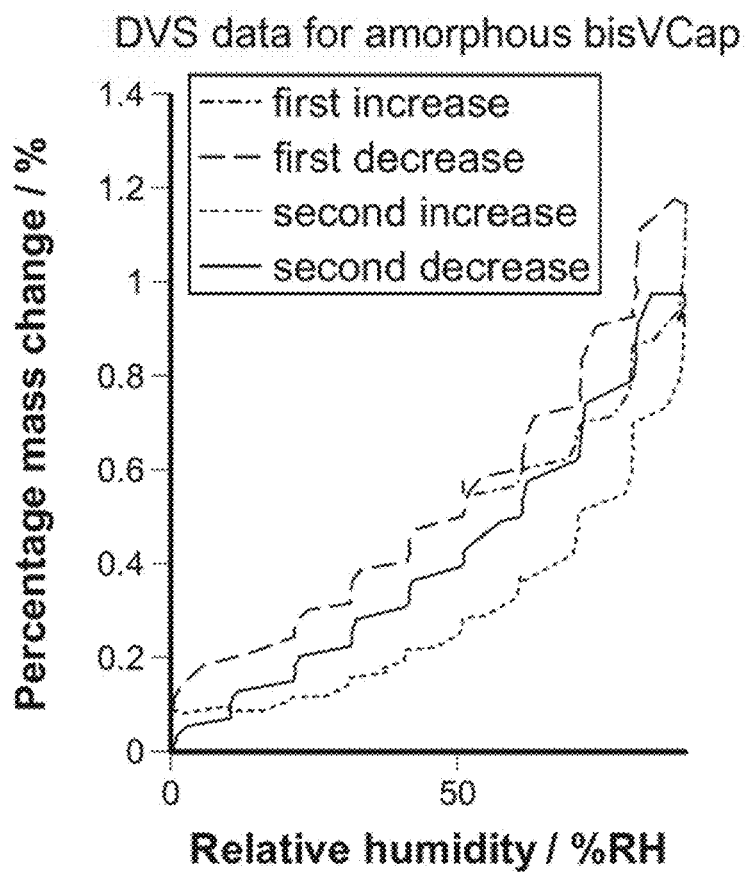

A significant issue with PVP as an amorphous stabilizer is its hydroscopicity, and amorphous materials are frequently hygroscopic. Dynamic vapor sorption (DVS) has been used to compare the water uptake of bisVCap and PVP. Unlike PVP, bisVCap is not hydroscopic and hence bisVCap may be a desirable amorphous stabilizer that is potentially less susceptible to absorption of atmospheric moisture. However, amorphous forms have more apparent solubility than crystal forms and it is possible that amorphous bisVCap could absorb much more water than the crystalline form. The DVS plot for crystalline bisVCap (FIG. 4a), shows a mass increase of 0.35% up to 90% relative humidity. Amorphous bisVCap (FIG. 4b), shows a larger mass increase of 1.2% over the same range, however this small increase in mass and lack of hysteresis in the DVS plot suggest that both crystalline and amorphous bisVCap are not significantly hygroscopic.

BisVCap appears to be a suitable small-molecule coamorphous phase former for a range of drugs, in some cases even at high drug-coformer ratio. Carisoprodol in particular showed promise, with a low loading of bisVCap and a long shelf life. BisVCap is also much less hygroscopic than PVP. The concept of adapting small-molecule analogs of known polymeric dispersions as coformers for coamorphous phases is a potentially interesting avenue for future work.

Experimental

Differential Scanning Calorimetry

Differential scanning calorimetry scans were recorded in standard mode on a TA Q2000 using standard aluminum pans containing 3-12 mg of sample. The heat/cool/heat cycles began with a heating cycle at a rate of 10° C. min$^{-1}$, then cooling cycle at 10° C. min$^{-1}$ and finally a second heating cycle at 10° C.

Dynamic Vapor Sorption

DVS was performed using an SMS DVS-1 with a 10% RH step between humidity values with equilibrium achieved at 0.01% weight change before moving to the next step. Methods began at the humidity of the room at ambient which was measured by a Rotronic A/H hygrometer. The humidity was then increased to 90% RH before cycling to 0% RH, to 90% RH, to 0% RH. Samples weighing between 5-20mg were used.

Hot Stage Microscopy

A Linkam LTS420 heating stage attached to a Olympus XC50 microscope was used to heat the samples. Samples were placed on a glass microscope slide with a thin glass cover slide. For the amorphous material screening compounds were ground together in various drug to coformer ratio using 0.05 g of coformer in each case and heated at 30° C. min$^{-1}$ until the all of the sample had melted. Samples were then removed from the hot stage and allowed to cool. BisVCap was ground in 1:1 molar mixture with carbamazepine, carisoprodol, isoniazid and ROY. The carbamazepine/bisVCap sample was heated from room temperature to 170° C. at a rate of 10° C. min$^{-1}$, cooled at ° C. min$^{-1}$ to −40° C., then heated at 10° C. min$^{-1}$ to 165° C. The carisoprodol/bisVCap sample was heated from room temperature to 150° C. at a rate of 10° C. min$^{-1}$, cooled at ° C. min$^{-1}$ to −75° C., then heated at 10° C. min$^{-1}$ to 145° C. min$^{-1}$. The isoniazid/bisVCap sample was heated from room temperature to 175° C. at a rate of 10° C. min$^{-1}$, cooled at ° C. min$^{-1}$ to −100° C., then heated at 10° C. min$^{-1}$ to 125° C. min$^{-1}$. The ROY/bisVCap sample was heated from room temperature to 150° C. at a rate of 10° C. min$^{-1}$, cooled at ° C. min$^{-1}$ to −90° C., then heated at 10° C. min$^{-1}$ to 155° C. min$^{-1}$.

Infrared Spectroscopy

Experiments were performed on a Perkin Elmer FTIR spectrum 100 with an attenuated total reflectance (ATR) attachment. Data were recorded at a resolution of 2 cm$^{-1}$ for 16 scans over the range 4000-600 cm$^{-1}$. Samples were run by placing on the ATR crystal and applying pressure using the side arm. Spectral analysis was performed using SpekWin32. Ground samples were prepared by grinding together in the desired ratio of the two components using a mortar and pestle for one minute. Melted samples were prepared by grinding together in the desired ratio of the two components using a mortar and pestle for one minute before placing the ground material into 5 mL glass vial with a plastic screw lid. After the lid was secured the sample was heated above the melting point of the highest melting component until everything had melted using a stirrer hotplate and appropriate heating block.

Crystallographic Analysis

X-ray powder diffraction patterns were recorded on a PANalytical Empyrean diffractometer using Cu Kα radiation (λ=1.54 Å), tube voltage of 40 kV and 40 mA current. Intensities were measured from 2° to 40° 2θ. Soller silts and an incident beam divergent slit of $\frac{1}{8}°$, anti-scatter slit of $\frac{1}{4}°$ and diffracted beam anti-scatter slit of 7.5 mm.

Materials and Methods

Compounds 3-7 were prepared according to previously published procedures. PVP K12 and PVCap were supplied by Ashland Inc. Compound 8 was prepared as detailed below.

N-vinyl(caprolactam) (2.0 g, 14.4 mmol) and hydroxyethylpyrrolidone (1.9 g, 14.4 mmol) were added to cyclohexane (10 cm$^3$) in a two neck round bottom flask with a reflux condenser. 0.5 cm$^3$ of TFA was added and the mixture was heated at 40° C. for 6 hours. The solvent was removed under vacuum to leave an orange oil. Unreacted N-vinyl (caprolactam) was removed using an alumina column with 75:25 diethylether:methanol mobile phase. The solvent was removed under vacuum and the resulting yellow oil was left in a vacuum desiccator under vacuum overnight to remove any remaining solvent residues. $^1$H NMR (400 MHz, D$_2$O) δ 5.58 (q, J=6.0 Hz, 1H), 3.54-3.37 (m, 6H), 3.37-3.28 (m, 1H), 3.23-3.15 (m, 1H) 2.63-2.42 (m, 2H), 2.35 (t, J=8.1 Hz, 2H), 2.00 (q, J=7.5 Hz, 2 H) 1.79-1.46 (m, 6H), 1.23 (d, J=6.0 Hz, 3H). $^{13}$C{$^1$H} NMR (101 MHz, CDCl$_3$) δ 176.70, 175.18, 79.33, 65.37, 48.34, 42.36, 40.96, 37.61, 30.82, 29.98, 29.26, 23.48, 19.19, 18.05. ESI-MS m/z 559 (2M+H$^+$, 100%), 269 (M+H$^+$, 58), 140 (45), 130 (36), 65 (14).

In the amorphous dispersions of this invention, the mole ratio of the active pharmaceutical ingredient to the lactam can range from about 1:1 to about 10:1, preferably 1:1 to 4:1 and more preferably 1:1 to 3:1.

What is claimed is:
1. An amorphous dispersion comprising
(a) a compound having a structure of

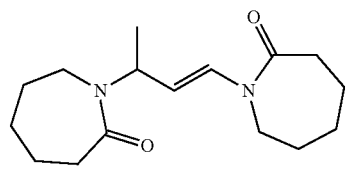 [SMILES: CC(/C=C/N1CCCCCC1=O)N1CCCCCC1=O]

and (b) an active pharmaceutical ingredient selected from the group consisting of benzocaine, caffeine, carbamazepine, carisoprodol, dopamine, ethionamide, ibuprofen, isoniazid, metformin, mexiletine, tolfenamic acid, valsartan, and ROY, wherein the mole ratio of said active pharmaceutical ingredient (b) to said compound (a) ranges from 1:1 to 3:1.

* * * * *